(12) United States Patent
Ferrant et al.

(10) Patent No.: US 8,059,900 B2
(45) Date of Patent: Nov. 15, 2011

(54) METHOD AND APPARATUS TO FACILITATE VISUALIZATION AND DETECTION OF ANATOMICAL SHAPES USING POST-PROCESSING OF 3D SHAPE FILTERING

(75) Inventors: Matthieu Denis Ferrant, Saint Rémy lès Chevreuse (FR); Saad Ahmed Sirohey, Pewaukee, WI (US); Paulo Ricardo dos Santos Mendonca, Clifton Park, NY (US); Jerome Knoplioch, Neuilly sur Seine (FR); Rahul Bhotika, Guilderland, NY (US)

(73) Assignee: General Electric Company, Schenectady, NY (US)

( * ) Notice: Subject to any disclaimer, the term of this patent is extended or adjusted under 35 U.S.C. 154(b) by 1423 days.

(21) Appl. No.: 10/961,245

(22) Filed: Oct. 8, 2004

(65) Prior Publication Data
US 2006/0079743 A1    Apr. 13, 2006

(51) Int. Cl.
*G06K 9/46* (2006.01)
(52) U.S. Cl. ....................................... 382/203
(58) Field of Classification Search ............ 382/203
See application file for complete search history.

(56) References Cited

U.S. PATENT DOCUMENTS

| | | | |
|---|---|---|---|
| 5,255,187 A | 10/1993 | Sorensen | |
| 5,823,993 A | 10/1998 | Lemelson | |
| 5,917,929 A | 6/1999 | Marshall et al. | |
| 6,266,435 B1 | 7/2001 | Wang | |
| 6,320,976 B1 * | 11/2001 | Murthy et al. | 382/128 |
| 6,434,262 B2 | 8/2002 | Wang | |
| 6,817,982 B2 * | 11/2004 | Fritz et al. | 600/443 |
| 6,865,300 B2 * | 3/2005 | Kokemohr | 382/260 |
| 6,983,063 B1 * | 1/2006 | Novak et al. | 382/131 |
| 7,024,027 B1 * | 4/2006 | Suri et al. | 382/130 |
| 2002/0150304 A1 * | 10/2002 | Ockman | 382/260 |
| 2004/0151356 A1 * | 8/2004 | Li et al. | 382/131 |

OTHER PUBLICATIONS

McCulloch, C. et al., "Reader Variability and Computer Aided Detection of Suspicious Lesions in Low-Dose CT Lung Screening Exams" Radiology 2003; 226(2): 37A.
Li, F. et al., "Lung Cancers Missed at Low-Dose Helical CT Screening in a Gen. Pop.: Comp. of Clinical, Histopathologic, and Imaging Findings" Radiology 2002; 225(3):673-683.
Kakinuma, R. et al., "Detection Failures in Spiral CT Screening for Lung Cancer: Analysis of CT Findings" Radiology 1999; 212: 61-66.

(Continued)

*Primary Examiner* — Daniel Mariam
*Assistant Examiner* — Elisa Rice
(74) *Attorney, Agent, or Firm* — Armstrong Teasdale LLP

(57) ABSTRACT

A method includes generating a first response including a plurality of potential first objects of interest of a first shape from data regarding a region of interest (ROI), generating a second response including a plurality of second objects of interest for a second shape different than the first shape from the data regarding the ROI, and performing a morphological closing on the second response to produce a second cleaned response including a plurality of completed second objects. The method also includes decreasing the number of potential objects of interest in the first response by deleting any potential first objects that overlap any completed second objects to obtain a cleaned first response, and generating an image using at least one of the first cleaned response and the second cleaned response.

24 Claims, 8 Drawing Sheets

OTHER PUBLICATIONS

Sato, Y et al, "Three-dimen. multi-scale line filter for segmentation and visualization of curvilinear structures in med. images," Med. Image Analysis, vol. 2, pp. 143-168, 1998.

Li, Q. et al., "Selective enhancement filters for nodules, vessels, and airway walls in two- and three-dimensional CT scans," Med. Phys., vol. 30, No. 8, pp. 2040-2051, 2003.

* cited by examiner (a)

(b)

(a)

(b)

METHOD AND APPARATUS TO FACILITATE VISUALIZATION AND DETECTION OF ANATOMICAL SHAPES USING POST-PROCESSING OF 3D SHAPE FILTERING

BACKGROUND OF THE INVENTION

This invention relates generally to methods and apparatus for review of medical imaging exams, and more particularly to methods and apparatus for review of computed tomographic (CT) colonography and lung exams.

CT imaging provides a description of anatomy in great detail and is therefore being increasingly used for detecting and following the evolution of lesions that may be potential cancers. Radiologists search for nodules and polyps in the lung and colon using advanced lung analysis (ALA) and Computed tomographic colonography (CTC). Lung Cancer and Colon Cancer are the first and third leading cause of cancer related mortality in the US with estimated 175,000 and 57,000 deaths in 2003. Many references in the literature point to better patient management from earlier detection.

Radiologists currently detect nodules in the lung by viewing the axial slices of the chest. This is time consuming and is getting more so with the resolution increase and hence the explosion of the amount of CT slices to be reviewed. For lung CT, detection is followed by an analysis for characterization of the nodule with the help of ALA's segmentation, volume measurement and reporting tools. During some of reader studies considerable variability in the detection of small nodules in lung scans by expert radiologists was found. In addition there are similar studies in the literature that describe a sensitivity issue when detecting nodules. Similar studies show reader variability in detecting polyps. Co-pending patent application Ser. No. 10/756,872 filed Jan. 12, 2004 (hereby incorporated in its entirety) describes using shape overlay information on the virtually dissected colon has been submitted to address better visualization of the colonic polyps. Another co-pending patent application Ser. No. 10/709,355 filed Apr. 29, 2004 (also hereby incorporated in its entirety) provides a real-time 3D shape filtering method to enhance certain geometrical features. These methods provide complementary shape information that can aid in the diagnosis of anatomical and/or clinical conditions. It was noted that providing simple raw results of the shape descriptors tended to overwhelm the user with either fragmented or at times false clinical information. Such information, even though an accurate representation of the filtering, should be presented to the user in a clinically efficient manner.

BRIEF DESCRIPTION OF THE INVENTION

In one aspect, a method is provided. The method includes generating a first response including a plurality of potential first objects of interest of a first shape from data regarding a region of interest (ROI), generating a second response including a plurality of second objects of interest for a second shape different than the first shape from the data regarding the ROI, and performing a morphological closing on the second response to produce a second cleaned response including a plurality of completed second objects. The method also includes decreasing the number of potential objects of interest in the first response by deleting any potential first objects that overlap any completed second objects to obtain a cleaned first response, and generating an image using at least one of the first cleaned response and the second cleaned response.

In another aspect, a method for generating an image is provided. The method includes receiving data regarding a scan of an anatomy, performing a first 3D shape filtering of the received data to generate at least two disparate responses, and generating a first merged image of the disparate responses.

In yet another aspect, a method for generating an image includes receiving data regarding a scan of an anatomy, performing a first 3D shape filtering of the received data, and generating a first image using the 3D shape filtered data. The method also includes displaying the generated image to a user to review, receiving from the user a response parameter, and generating a second image using the received response parameter.

In still another aspect, a method for obtaining data is provided. The method includes scanning an anatomy to acquire data, and determining at least one local curvature around a null space of a gradient of the acquired data.

In another aspect, a method for obtaining data includes scanning an anatomy to acquire data, and determining a plurality of principal directions of a local distribution of gradients.

In yet another aspect, a method for obtaining data includes accessing scan data, generating a plurality of responses using the accessed scan data, and, from the responses, classifying a plurality of regions according to shape. The method also includes performing a cluster analysis, determining a center of gravity for each cluster, and performing an auto-segmentation based upon the determined center of gravity.

In still another aspect, an imaging system is provided. The imaging system includes means for accessing data, and a computer operationally coupled to the means. The computer is configured to generate a first response including a plurality of potential first objects of interest of a first shape from data regarding a region of interest (ROI), generate a second response including a plurality of second objects of interest for a second shape different than the first shape from the data regarding the ROI, and perform a morphological closing on the second response to produce a second cleaned response including a plurality of completed second objects. The computer is also configured to decrease the number of potential objects of interest in the first response by deleting any potential first objects that overlap any completed second objects to obtain a cleaned first response, and generate an image using at least one of the first cleaned response and the second cleaned response.

In yet another aspect, a computer readable medium encoded with a program is provided. The program is configured to instruct a computer to receive data regarding a scan of an anatomy, perform a first 3D shape filtering of the received data to generate at least two disparate responses, and generate a first merged image of the disparate responses.

In another aspect, a computer readable medium encoded with a program is provided. The program is configured to instruct a computer to receive data regarding a scan of an anatomy, perform a first 3D shape filtering of the received data, generate a first image using the 3D shape filtered data, and display the generated image to a user to review. The program is also configured to instruct a computer to receive from the user a response parameter, and generate a second image using the received response parameter.

In still another aspect, an imaging system is provided. The imaging system includes means for accessing data, and a computer operationally coupled to the means. The computer is configured to scan an anatomy to acquire data, and determine at least one local curvature around a null space of a gradient of the acquired data.

In another aspect, a computer readable medium encoded with a program is provided. The program is configured to instruct a computer to access scan data, generate a plurality of responses using the accessed scan data, and, from the responses, classify a plurality regions according to shape. The program is also configured to instruct the computer to perform a cluster analysis, determine a center of gravity for each cluster, and perform an auto-segmentation based upon the determined center of gravity.

DETAILED DESCRIPTION OF THE INVENTION

Figure 1:
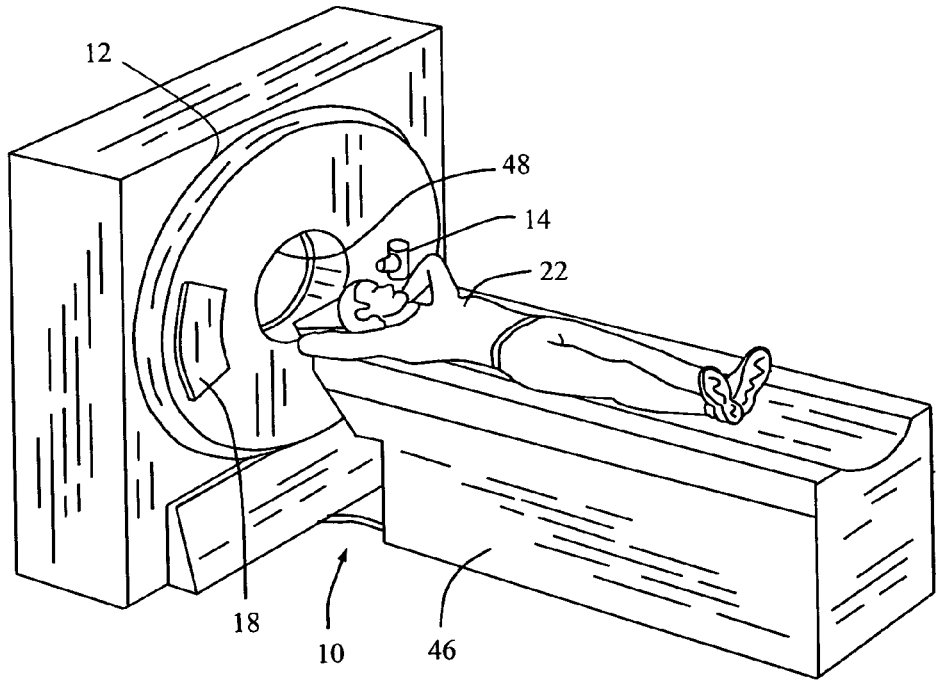
FIG. 1 is a pictorial view of a CT imaging system embodiment.

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to reconstruct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image. Additionally, although described in detail in a CT medical setting, it is contemplated that the benefits accrue to all imaging modalities including, for example, ultrasound, Magnetic Resonance Imaging, (MRI), Electron Beam CT (EBCT), Positron Emission Tomography (PET), Single Photon Emission Computed Tomography (SPECT), and in both medical settings and non-medical settings such as an industrial setting or a transportation setting, such as, for example, but not limited to, a baggage scanning CT system for an airport or other transportation center.

Figure 2:
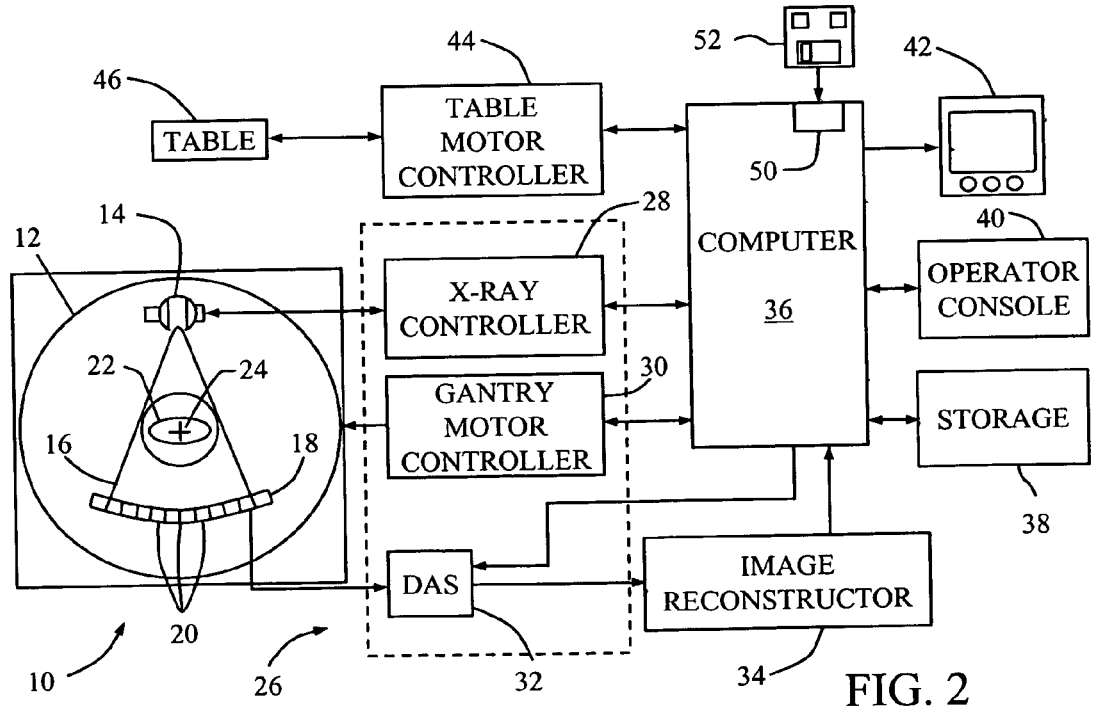
FIG. 2 is a block schematic diagram of the system illustrated in FIG. 1.

FIG. 1 is a pictorial view of a CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system. Gantry 12 has a radiation source 14 that projects a cone beam 16 of X-rays toward a detector array 18 on the opposite side of gantry 12.

Detector array 18 is formed by a plurality of detector rows (not shown) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Generally, a processor in at least one of DAS 32, reconstructor 34, and computer 36 shown in FIG. 2 is programmed to execute the processes described below. Of course, the method is not limited to practice in CT system 10 and can be utilized in connection with many other types and variations of imaging systems. In one embodiment, Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Figure 3:
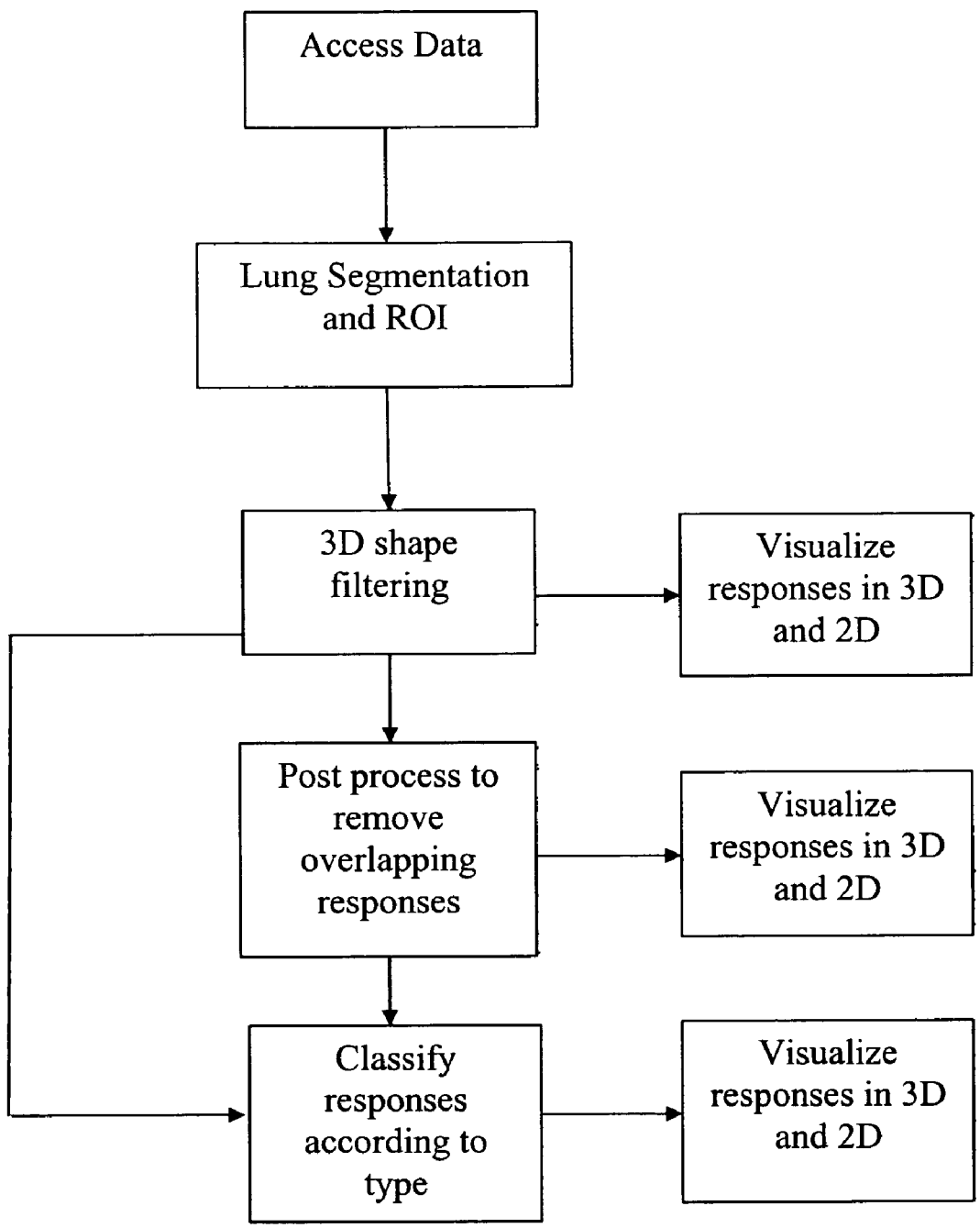
FIG. 3 describes an interaction of components.
Figure 4:
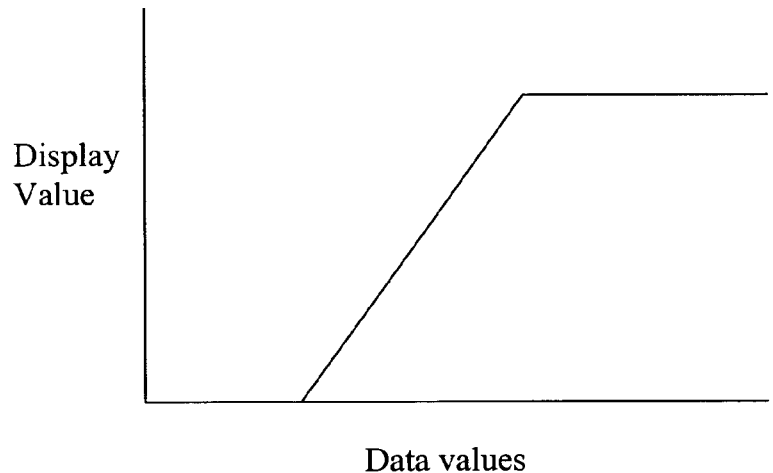
FIG. 4 illustrates a transfer function.
Figure 4:
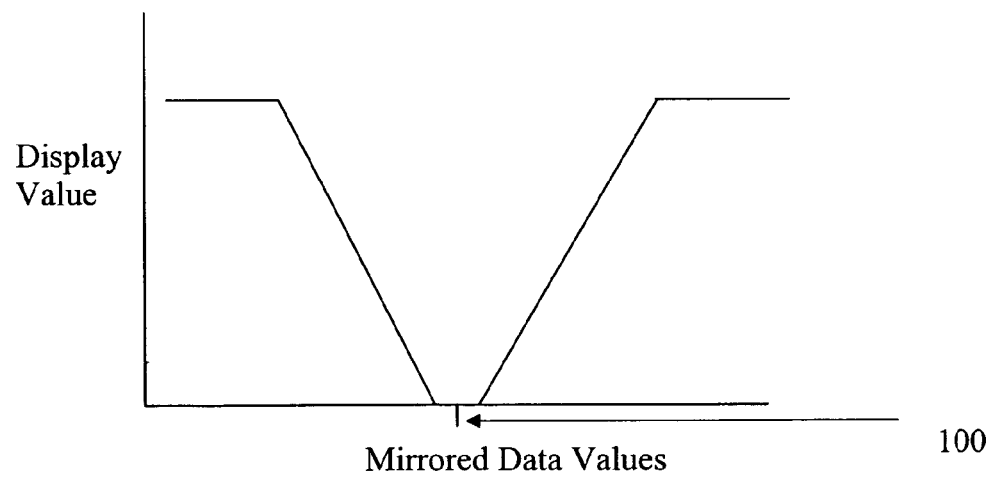

The herein described methods and apparatus are separable into three main categories all relating to post-processing of 3D shape filtering. These categories are a) apparatus and methods for displaying the combination of disparate shape responses and their response magnitude in a user interactive manner, b) apparatus and methods that reduce the overlap of disparate responses by post-processing the responses using a-priori anatomical knowledge and morphological operations and c) apparatus and methods that use classifying algorithms to reduce erroneous responses. The different categories and their combinations are depicted in FIG. 3. Each of these categories will be described in detail individually. FIG. 3 describes the interaction of these components. These methods and apparatus facilitates the ability to detect and visualize nodules in the lung and polyps in the colon but it should be noted that the specific anatomy or pathology concerned are for illustrative purposes only and people familiar with the art can clearly appreciate its application for a broad range of domain. In its simplest form the herein described apparatus and methods can be summed up in the ability to post process disparate responses (eg. spherical and cylindrical) using a-priori anatomical information to minimize the cross pollution of the responses and/or using response classification algorithms to reduce the size of the cross pollution followed by a visualization process that displays the responses using response magnitude and innovative window and level feature on the response magnitude.

a) Visualization of Responses: The output of the 3D filtering can be segregated into different response types depending on the task at hand. In one exemplary illustration the segregation may be in the form of a degree of cylindricalness or sphericalness of the underlying object. The response of this filtering may also have an underlying scale component that creates equivalence to both the size and the shape of the underlying object, i.e. the filtering may be tuned to respond maximally to cylinders (and spheres) that have a diameter of 8 mm and being non-maximal if the underlying object deviates in size or shape from the desired tuned value. The shape responses may be displayed independently or overlaid on the image data represented in either 2D or volumetric 3D rendering. A method similar to the currently available Window and Level (W/L) operation is applied to the filtered responses that allow the user to selectively display the responses that they want to see, in essence providing the user with the ability to tune the sensitivity to non-maximal responses. This method can be applied independently to the filtering responses. Another innovative method is the merging of disparate responses for a combined display without loosing the ability for the user to W/L. This ability was achieved using two complementary methods, the first created an artificial datum point in response space that allowed the response data to be segregated in a mirrored sense about this datum and the second used similarly mirrored color map with appropriate transfer functions. The result of these methods is that the user can apply the selective W/L and the disparate responses of the filtering (e.g. spherical and cylindrical) are simultaneously displayed independently or on the image data using their own color map for visual distinction. The transfer function is illustrated in FIG. 4. FIG. 4(a) illustrates a standard linear look up table (LUT) and 4(b) utilizes the mirrored spherical and cylindrical response with a mirrored LUT to display disparate responses simultaneously using the same user interactions as in (a).

b) An innovative method is described to reduce the overlap of the disparate responses by using a-priori anatomical information. For the illustrative example of the lung, the 3D responses are determined using either the method described in Sato, Y et. al. "Three-Dimensional multi-scale line filter for segmentation and visualization of curvilinear structures in medical images", Medical Image Analysis, Vol. 2, pp 143-168, 1998. or Li, Q., Sone, S., and Doi, K, "Selective enhancement filters for nodules, vessels, and airway walls in two- and three-dimensional CT scans", Med. Phys. Vol. 30, No 8, pp 2040-2051, 2003 with an optimized implementation (as described in co-pending application Ser. No. 10/709,355) or a new formulation using local curvature at implicit isosurfaces. The new method termed curvature tensor determines the local curvatures Kmin and Kmax in the null space of the gradient. The respective curvatures can be determined using the following formulation:

$$k_i = (\min \hat{v}, \max \hat{v}) \frac{-\hat{v}^T N^T H N \hat{v}}{\|\nabla I\|} \quad (1)$$

where k is the curvature, v is a vector in the N null space of the gradient of image data I with H being its Hessian. The solution to equation 1 are the eigen values of the following equation:

$$\frac{-N^T H N}{\|\nabla I\|} \quad (2)$$

The responses of the curvature tensor (Kmin and Kmax) are segregated into spherical and cylindrical responses based on thresholds on Kmin, Kmax and the ratio of Kmin/Kmax derived from the size and aspect ratio of the sphericalness and cylindricalness that is of interest, in one exemplary formulation the aspect ratio of 2:1 and a minimum spherical diameter of 1 mm with a maximum of 20 mm is used. It should be noted that a different combination would result in a different shape response characteristic that would be applicable for a different anatomical object. It should also be noted that a structure tensor can be used as well. The structure tensor is used in determining the principal directions of the local distribution of gradients. Strengths (Smin and Smax) along the principal directions can be calculated and the ratio of Smin and Smax can be examined to segregate local regions as a spherical response or a cylindrical response similar to using Kmin and Kmax above.

Figure 5:
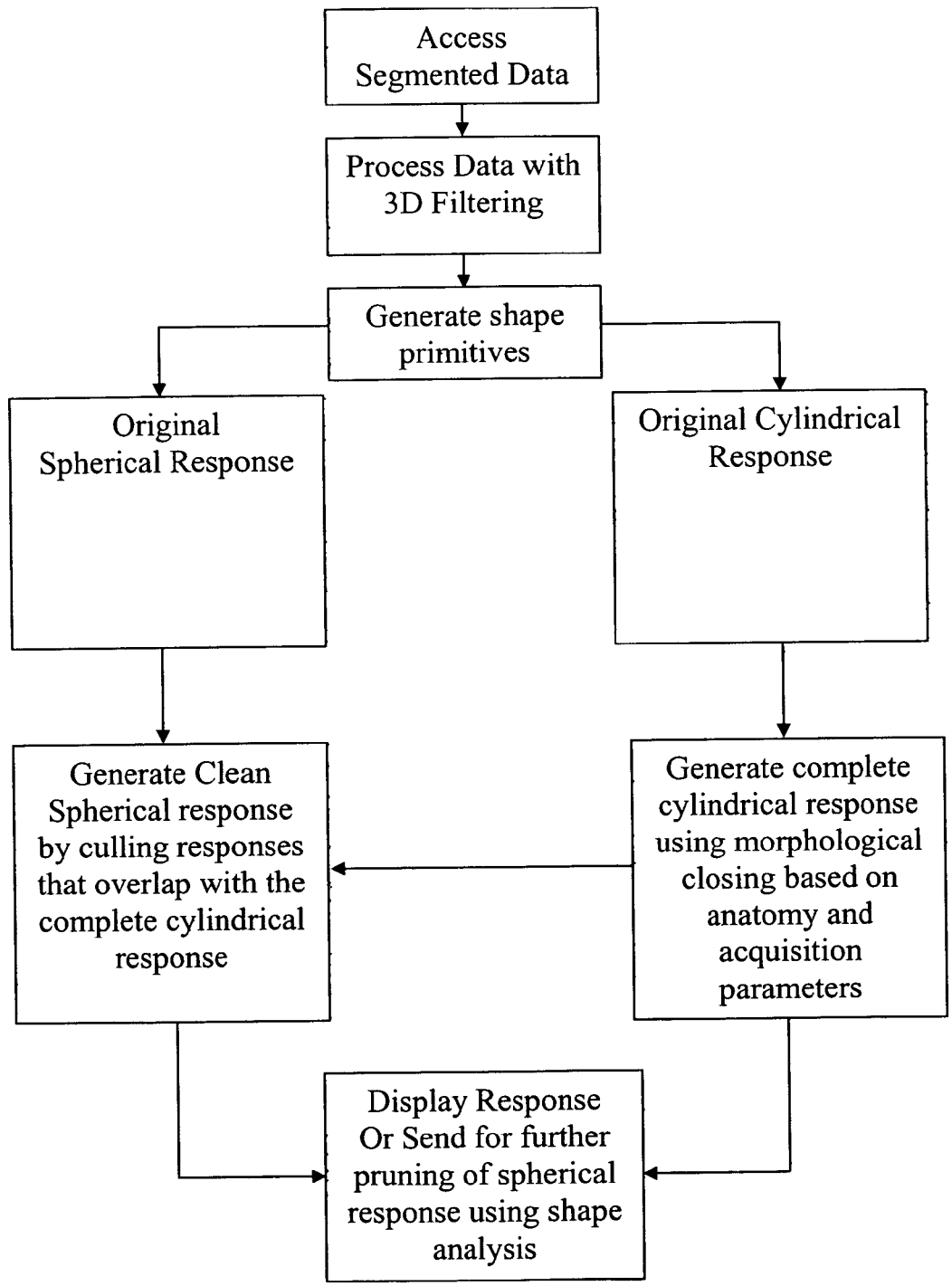
FIG. 5 illustrates a process for masking out false responses using complementary information.
Figure 8:
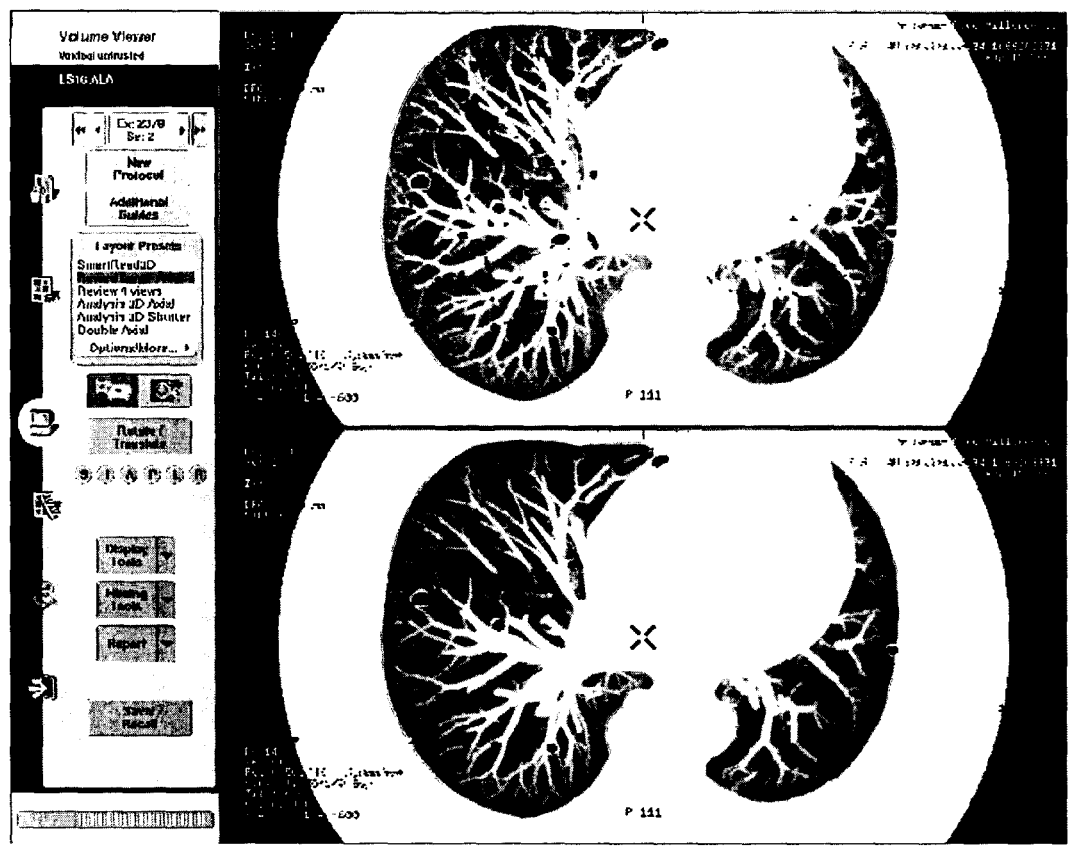
FIG. 8 illustrates example results.
Figure 9:
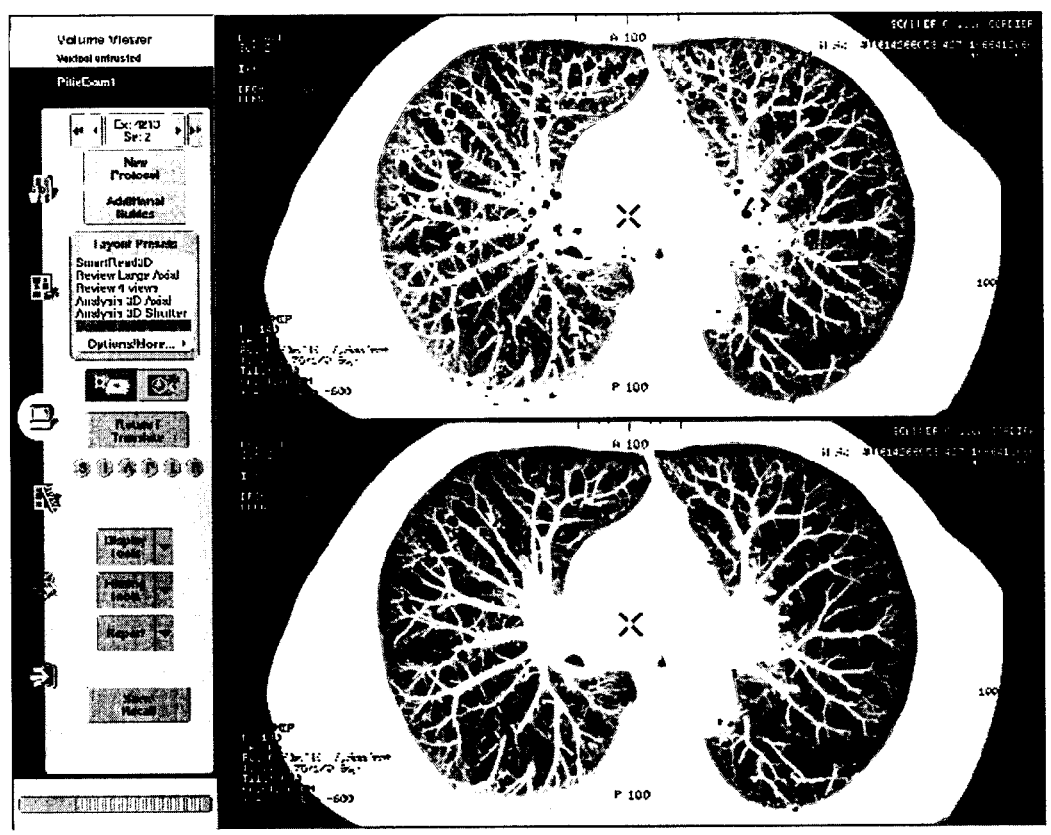
FIG. 9 illustrates example results.
Figure 10:
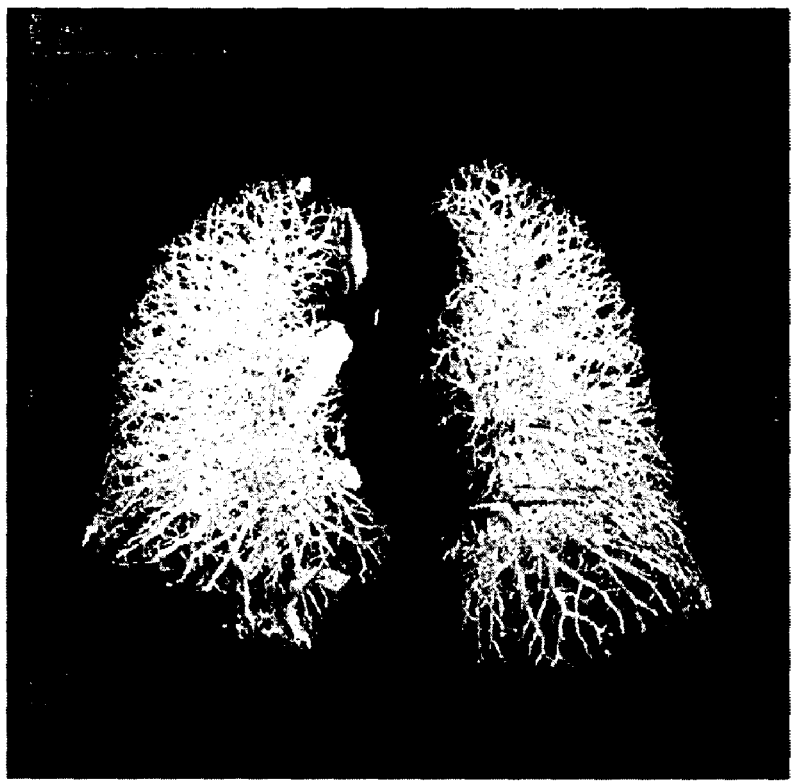
FIG. 10 illustrates example results.
Figure 10:

The disparate responses so established do have overlapping regions that can be termed as false responses. The differing acquisition parameters and reconstruction algorithm and their noise characteristics are a major source of these false responses. A method of removing the false responses would be to tweak the threshold values to compensate for the differing acquisitions. This would involve creating a mapping of the thresholds to all possible acquisition which is an intractable problem. One solution to the problem lies in utilizing anatomical information in the form of the scale of the responses on large vessels (cylindrical responses) and the intentional biasing of a response towards spherical vs. cylindrical to come up with the use of morphological closing of the cylindrical response volume to cull any spherical responses that are in the intersection of the "closed" cylindrical responses and the spherical response. This procedure is illustrated in FIG. 5. FIG. 5 illustrates a process for masking out false responses using complementary information. A comparative view of this algorithm with the version described in co-pending application Ser. No. 10/709,355 can be seen in FIG. 10. Note the dramatic reduction of responses in FIG. 10(b) compared to FIG. 10(a). In comparative tests a noticeable improvement in sensitivity with a dramatic reduction of false responses (typically at junctions) was observed. Referring back to FIG. 5, segmented data is accessed. The data is processed with 3D filtering and shape primitives are generated resulting an original spherical response and an original cylindrical response. Morphological closing id performed on the original cylindrical response to generate a cleaned response including a plurality of complete cylinders. The cleaned response can then be displayed if desired. Also the cleaned cylindrical response can be analyzed in coordination with the original spherical response. In other words, a clean spherical response can be generated culling original responses that overlap with completed cylinders. The clean spherical response can be displayed and/or sent to a shape analysis module for further pruning of individual spherical responses. Referring back to FIG. 10, FIG. 10(a) shows spherical responses of the Hessian based filter. FIG. 10(b) shows the same image with the responses of the curvature tensor that are post processed using morphological closing and masking based on the cylindrical responses. Note the marked reduction of the false responses on the junction of vessels.

c) The third part of these herein described methods and apparatus is a new methodology for the automated reduction of false positives in lung nodules and colon polyps detection in CT images while maintaining very high sensitivity. The method proceeds after a first rough filtering and candidate selection has been performed. In a first step a global filtering is applied so as to enhance the lesions, and as a second step a localized shape analysis is made for each candidate to determine whether it is an actual lesion or a false positive. For lung nodules, the first step can be a hessian analysis such as described in a previous application Ser. No. 10/709,355, which provides a very high sensitivity but a significant amount of false positives, or curvature analysis with post-processing such as described in the previous section). The second step can then be executed by attempting a simplified lung nodule segmentation (as used for sizing nodules in ALA for instance) on each candidate. This is valid for any nodule type (isolated, juxta-vascular or juxta-pleural) but also for any nodule consistency (solid, non-solid or part-solid). Preliminary internal studies have shown that this approach decreases the amount of false positives by 75% and more without compromising sensitivity. Typical results of such a processing are illustrated in FIGS. 8 and 9. An identical scheme can be followed for the automated detection of colon polyps using curvature estimates to select polyp candidates. FIG. 8 illustrates a 20 mm MIP (Maximum Intensity Projection) slab of a lung with standard reconstruction algorithm. The upper viewport shows an overlay of a standard Hessian filtering after thresholding. Note the false positives on the vessel junctions and around the hilum. The lower viewport shows same view after processing of all hessian filtering responses using ALA segmentation. Note that no vessel junctions or other false positives remain after the processing. FIG. 9 illustrates another example of a 20 mm MIP slab of a lung with a lung reconstruction algorithm. The upper viewport shows an overlay of a standard Hessian filtering after thresholding. Note the false positives on the vessel junctions and around the hilum. The lower viewport is the same view after processing of all hessian filtering responses using ALA segmentation. Note that no vessel junctions or other false positives remain after the processing.

The present description refers to lesions to be found in CT images of the lung or the colon, but could be applied to other organs and/or imaging modalities where it is desirable to detect suspicious lesions.

Figure 6:
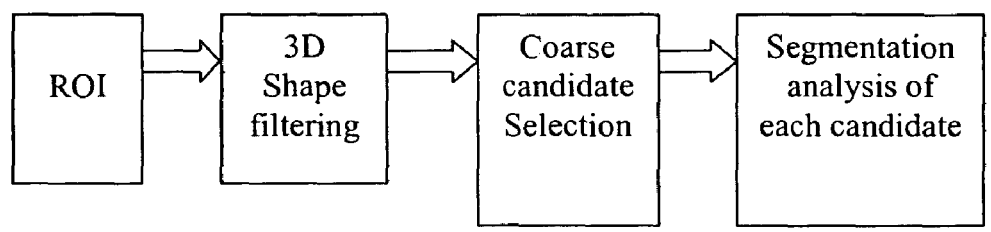
FIG. 6 illustrates an exemplary workflow of one innovative aspect of a method.

An exemplary workflow of the innovative aspect of the method is illustrated in FIG. 6.

Figure 7:
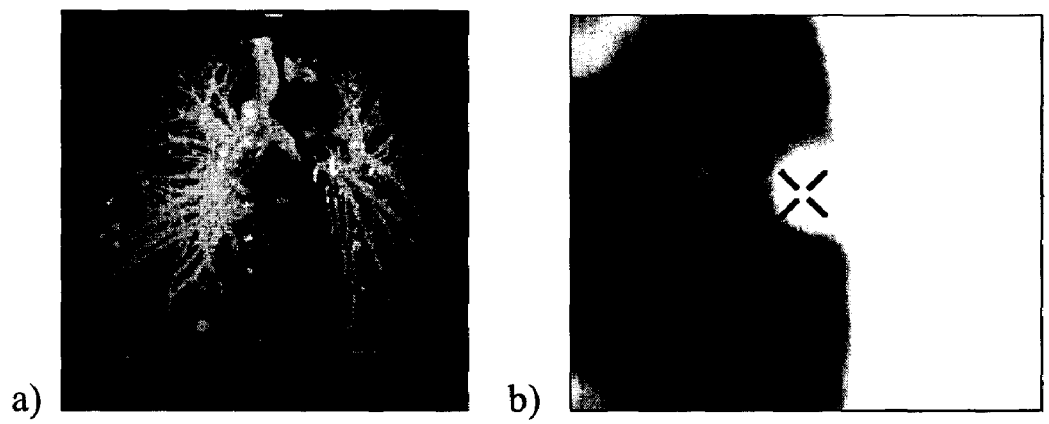
FIG. 7 illustrates example results.
Figure 7:
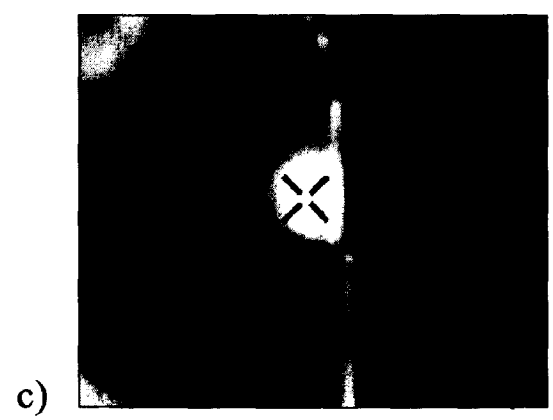

1. Extract ROI (lungs or colon): this step speeds up further computations, and helps further processing as juxta-pleural nodules can then be considered as isolated or juxta-vascular nodules (see FIG. 7 for example). FIG. 7 illustrates a) an example of a Lung ROI, b) a close-up of a juxtapleural nodule in original image and c) a close-up of the juxtapleural nodule after the lung ROI extraction. Notice that the juxtapleural nodule can now be treated as an isolated nodule.

2. Filter ROI using 3D shape computations: based upon eigenvalue of Hessian analysis or curvature computations.

3. Coarsely process response volume so as to reduce very small responses in size (amount of voxels) and intensity, or using complementary response volumes to eliminate very unlikely positive responses 4. Process the center of gravity of each remaining cluster of the response volume by placing a seed and running a localized shape analysis algorithm (e.g. ALA segmentation algorithm). Depending on the result of the segmentation (success/failure) the cluster is kept or removed from the coarsely processed response volume.

Point 1) has already been described in patent application Ser. No. 10/709,355.

2) 3D Shape computations, can be done as is described in patent application Ser. No. 10/709,355 using eigenvalue analysis or using efficient computations of the principal curvatures and analysis of these curvatures.

3) Coarse Processing of response analysis, this can be done in two main different ways that can possibly be combined:

1. Eliminate clusters of responses whose response level are below a certain threshold and/or whose size is below a chosen threshold.

2. Exploit orthogonality of different shape response types to remove false positives. For instance, using the principal curvature responses, sphericalness is orthogonal to cylindricalness. By processing imperfections of the cylindricalness (using a morphological closing for instance) and masking out sphericalness responses covered by cylindricalness responses one can actually reduce the number of false positive responses (see part (b) for more details).

4) Localized Shape Analysis, this step includes analyzing the center of mass of each cluster of responses at this stage, and apply a localized advanced shape analysis in order to determine whether this cluster of voxels is an actual lesion or not. FIGS. 8 and 9 illustrate the results such an approach yields for lung nodules using ALA's segmentation algorithm to do the localized shape analysis.

One technical effect of the herein described methods and apparatus is the simultaneous display of a plurality of synchronized views facilitating providing users examination results in an easy, user friendly environment.

While the invention has been described in terms of various specific embodiments, those skilled in the art will recognize that the invention can be practiced with modification within the spirit and scope of the claims.

What is claimed is:

1. A method for generating an image, said method comprising:
   receiving data regarding a scan of an anatomy;
   performing a first 3D shape filtering of the received data to generate at least two disparate responses, wherein the disparate responses include a cylindrical response and a spherical response; and
   generating a first merged image of the disparate responses, wherein generating the first merged image comprises eliminating false responses from a plurality of responses in the spherical response using the cylindrical response; and
   displaying the generated first merged image to a user.

2. A method in accordance with claim 1 further comprising creating an artificial datum point in a response space.

3. A method in accordance with claim 2 further comprising segregating response data in a mirrored fashion about the datum point.

4. A method in accordance with claim 1 wherein said generating comprises generating an image wherein a first response is in a first color and a second response different from the first response is in a second color different from the first color.

5. A method in accordance with claim 1 further comprising:
   receiving from a user a response parameter; and
   generating a second merged image of the disparate responses using the received parameter.

6. A method for generating an image, said method comprising:
   receiving data regarding a scan of an anatomy;
   performing a first 3D shape filtering of the received data, wherein performing the 3D shape filtering comprises generating a spherical response and a cylindrical response of the received data;
   generating a first image using the 3D shape filtered data, wherein generating the first merged image comprises eliminating false responses from a plurality of responses in the spherical response using the cylindrical response;
   displaying the generated image to a user to review;
   receiving from the user a response parameter, wherein the response parameter includes at least one of a spherical response and a cylindrical response; and
   generating a second cleaned image using the received response parameter.

7. A method in accordance with claim 6 wherein said receiving from the user comprises receiving from the user a response type, said generating a second image comprises generating a second image using the received response type.

8. A method in accordance with claim 6 wherein said generating a second image comprises generating a second image using the received response parameter.

9. A method in accordance with claim 6 wherein said receiving from the user comprises receiving from the user a percentage of response type match, said generating a second image comprises generating a second image using the received percentage.

10. A method in accordance with claim 6 wherein said receiving from the user comprises receiving from the user a size, said generating a second image comprises generating a second image using the received size.

11. A method in accordance with claim 6 wherein said receiving from the user comprises receiving from the user a scale, said generating a second image comprises generating a second image using the received scale.

12. A method in accordance with claim 6 wherein said generating a second image comprises performing a second 3D shape filtering of the received data using the received response parameter.

13. A method in accordance with claim 12 wherein said receiving from the user comprises receiving from the user a response type, said performing a second 3D shape filtering comprises performing a second 3D shape filtering of the received data using the received response parameter.

14. A method in accordance with claim 12 wherein said receiving from the user comprises receiving from the user a response type including at least one of a spherical response and a cylindrical response, said performing a second 3D shape filtering comprises performing a second 3D shape filtering of the received data using the received response parameter.

15. A method in accordance with claim 12 wherein said receiving from the user comprises receiving from the user a percentage of response type match, said performing a second 3D shape filtering comprises performing a second 3D shape filtering of the received data using the received percentage.

16. A method in accordance with claim 12 wherein said receiving from the user comprises receiving from the user a size, said performing a second 3D shape filtering comprises performing a second 3D shape filtering of the received data using the received size.

17. A method in accordance with claim 12 wherein said receiving from the user comprises receiving from the user a scale, said performing a second 3D shape filtering comprises performing a second 3D shape filtering of the received data using the received scale.

18. A non-transient computer readable medium encoded with a program configured to instruct a computer to:
   receive data regarding a scan of an anatomy;
   perform a first 3D shape filtering of the received data to generate at least two disparate responses, wherein disparate responses include a cylindrical and a spherical response; and
   generate a first merged image of the disparate responses wherein generating the first merged image comprises eliminating false responses from a plurality of responses in the spherical response using the cylindrical response.

19. A medium in accordance with claim 18 wherein said program further configured to instruct the computer to generate an image wherein a first response is in a first color and a second response different from the first response is in a second color different from the first color.

20. A medium in accordance with claim 18 wherein said program further configured to instruct the computer to:
  generate a second merged image of the disparate responses using the received parameter.

21. A non-transient computer readable medium encoded with a program configured to instruct a computer to:
  receive data regarding a scan of an anatomy;
  perform a first 3D shape filtering of the received data, wherein performing the 3D shape filtering comprises generating a spherical response and a cylindrical response of the received data;
  generate a first image using the 3D shape filtered data, wherein generating the first merged image comprises eliminating false responses from a plurality of responses in the spherical response using the cylindrical response;
  display the generated image to a user to review;
  receive from the user a response parameter including at least one of the spherical response and the cylindrical response; and
  generate a second image using the received response parameter.

22. A medium in accordance with claim 21 wherein said program further configured to instruct the computer to:
  receive from the user a percentage of response type match; and
  generate the second image using the received percentage.

23. A medium in accordance with claim 21 wherein said program further configured to instruct the computer to:
  receive from the user a size; and
  perform a second 3D shape filtering of the received data using the received size.

24. A medium in accordance with claim 21 wherein said program further configured to instruct the computer to:
  receive from the user a scale; and
  perform a second 3D shape filtering of the received data using the received scale.

* * * * *